US00PP27277P3

(12) United States Plant Patent
Grosser

(10) Patent No.: US PP27,277 P3
(45) Date of Patent: Oct. 18, 2016

(54) ***CITRUS* ROOTSTOCK NAMED 'UFR-1'**

(50) Latin Name: *Citrus reticulata/Citrus paradisi+Citrus grandis×Citrus reticulata+Poncirus trifoliata*
Varietal Denomination: UFR-1

(71) Applicant: Florida Foundation Seed Producers, Inc., Marianna, FL (US)

(72) Inventor: Jude W. Grosser, Winter Haven, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 0 days.

(21) Appl. No.: 14/544,572

(22) Filed: Jan. 22, 2015

(65) Prior Publication Data

US 2015/0237782 P1 Aug. 20, 2015

Related U.S. Application Data

(60) Provisional application No. 61/942,571, filed on Feb. 20, 2014.

(51) Int. Cl.
*A01H 5/00* (2006.01)

(52) U.S. Cl.
USPC ..... Plt./201

(58) Field of Classification Search
USPC ..... Plt./201
See application file for complete search history.

(56) References Cited

U.S. PATENT DOCUMENTS

PP21,535 P2 11/2010 Grosser

OTHER PUBLICATIONS

PLUTO: Plant Variety Database, Jan. 13, 2015, citation for 'UFR-1'. 1 page.*
U.S. Appl. No. 14/544,423, filed Jan. 5, 2015, Grosser.
U.S. Appl. No. 14/544,424, filed Jan. 5, 2015, Grosser.
U.S. Appl. No. 14/544,425, filed Jan. 5, 2015, Grosser.
U.S. Appl. No. 14/544,427, filed Jan. 5, 2015, Grosser.
U.S. Appl. No. 14/544,570, filed Jan. 22, 2015, Grosser.
U.S. Appl. No. 14/544,571, filed Jan. 22, 2015, Grosser.
U.S. Appl. No. 14/544,573, filed Jan. 22, 2015, Grosser.
U.S. Appl. No. 14/545,063, filed Mar. 20, 2015, Grosser.
Grosser et al., "Protoplast fusion and citrus improvement," *Plant Breeding Reviews* 8:339-374, 1990.
Grosser et al., "Development of "tetrazyg" rootstocks tolerant of the diaprepes/phytophthora complex under greenhouse conditions," *Proc. Fla. State Hort. Soc.* 116:263-267, 2003.
Grosser et al., "Continued Development of Rootstocks Tolerant of the *Phytophthora*-Diaprepes Complex via Greenhouse Screening," *Proc. Fla. State Hort. Soc.* 120:103-109, 2007.
Grosser et al., "Salinity tolerance of 'Valencia' orange trees on allotetraploid rootstocks," *Proc. Fla. State Hort.* 125:50-55, 2012.
Grosser et al., "Protoplast fusion for production of tetraploids and triploids: Applications for scion and rootstock breeding in citrus," *Plant Cell Tissue Organ Culture* 104:343-357, 2011.

* cited by examiner

*Primary Examiner* — Susan McCormick Ewoldt
*Assistant Examiner* — Karen Redden
(74) *Attorney, Agent, or Firm* — Dentons US LLP

(57) ABSTRACT

'UFR-1' is a new and distinct allotetraploid citrus rootstock for tree size control and improved disease resistance. 'UFR-1' has shown a positive reaction to the Huanglongbing disease (HLB, or citrus greening disease) in multiple experimental field trials. Scion trees grafted on this rootstock show a reduced frequency of infection and reduced disease symptoms once infected as compared to commercial diploid rootstocks.

6 Drawing Sheets

1

BACKGROUND OF THE INVENTION

Latin name of the genus and species of the plant claimed: *Citrus reticulata/Citrus paradisi+Citrus grandis×Citrus reticulata+Poncirus trifoliata.*

Variety denomination: 'UFR-1'.

The present invention relates to a new and distinct variety of citrus rootstock named 'UFR-1'. The Plant Improvement Team in Lake Alfred, Fla. has pioneered the development and testing of allotetraploid citrus rootstocks. 'UFR-1' (identified as Orange #3 in field trials) is an allotetraploid zygotic hybrid derived from a conventional cross of two somatic hybrids previously produced by protoplast fusion. The somatic hybrid seed parent is 'Nova' mandarin hybrid+'Hirado Buntan' pummelo (zygotic seedling), and the somatic hybrid pollen parent is 'Cleopatra' mandarin+'Argentine' trifoliate orange.

2

BRIEF SUMMARY OF THE INVENTION

'UFR-1' was selected as a potential citrus rootstock on the basis of its positive reaction to Huanglongbing disease (HLB, or citrus greening disease) in multiple experimental field trials. Scion trees grafted onto 'UFR-1' showed a reduced frequency of infection and reduced disease symptoms once infected when compared to other commercial diploid rootstocks. Although scion trees grafted onto 'UFR-1' grow off quickly, the trees remain small in size, making 'UFR-1' suitable for use in Advanced Citrus Production Systems that feature high density plantings. 'UFR-1' produces adequate nuclear seed, making it amenable to standard nursery propagation practices for uniform liner production. 'UFR-1' exhibited salinity tolerance in a greenhouse study (Grosser et al., 2012), and tolerance of the *Diaprepes/*

*Phytophthora* complex in a separate greenhouse study (Grosser et al., 2003). Long-term performance of trees on this rootstock selection is unknown. Yield and fruit quality data is limited, but 3 years of data from young trees (the St. Helena project, see Table 1) indicates good productivity and fruit quality. Tolerance to citrus blight is also unknown, but under investigation. True-to-typeness through asexual reproduction was demonstrated by topworking 'UFR-1' onto a 'Carrizo' citrange rootstock in Lake Alfred, Fla. Seed from this topworked tree and from the original tree are predominantly of nucellar origin, producing true-to-type seedlings.

TABLE 1

Rootstock Data from 5-year old trees in the St. Helena trial - Dundee, FL.

| | | | Lbs Solids/Box | |
|---|---|---|---|---|
| Scion | Type | Rootstock | 2012 | 2013 |
| VALQUARIUS | Som. Hyb. | 'UFR-6' | 5.64 | 5.43 |
| VERNIA | Som. Hyb. | 'UFR-6' | 5.67 | 6.01 |
| VALQUARIUS | Tetrazyg | 'UFR-1' | 5.5 | 4.87 |
| VERNIA | Tetrazyg | 'UFR-1' | 5.61 | 6.28 |
| VERNIA | Tetrazyg | 'UFR-2' | 5.47 | 5.93 |
| VALQUARIUS | Tetrazyg | 'UFR-2' | 4.57 | 5.37 |
| VALQUARIUS | Tetrazyg | 'UFR-3' | 4.84 | 5.05 |
| VERNIA | Tetrazyg | 'UFR-3' | 5.46 | 5.82 |
| VERNIA | Tetrazyg | 'UFR-4' | 5.79 | 6.07 |
| VALQUARIUS | Tetrazyg | 'UFR-4' | 4.65 | 5.07 |
| VALQUARIUS | Tetrazyg | 'UFR-5' | 5.76 | 5.72 |
| VERNIA | Tetrazyg | 'UFR-5' | 5.89 | 5.34 |
| VALQUARIUS | Diploid | FG 1731 | 5.83 | 6.81 |
| VALQUARIUS | Diploid | FG 1733 | 5.12 | 5.63 |
| VERNIA | Diploid | SWINGLE* | 5.11 | 5.79 |
| VALQUARIUS | Diploid | SWINGLE* | NS | 5.61 |
| VERNIA | Diploid | CLEO* | 4.79 | 5.51 |
| VALQUARIUS | Diploid | CLEO* | NS | 5.21 |
| VERNIA | Diploid | R. LEMON* | 3.67 | na |
| VALQUARIUS | Diploid | VOLK* | NS | 4.12 |
| VERNIA | Diploid | VOLK* | 3.6 | 4.73 |
| VALQUARIUS | Diploid | KUHARSKE* | NS | 5.75 |
| VERNIA | Diploid | KUHARSKE* | 4.34 | 5.83 |

| | Yield Boxes/Tree | | | Cumulative |
|---|---|---|---|---|
| Scion | 2011 (35 mo.) | 2012 (47 mo.) | 2013 (59 mo.) | Yield (Boxes) |
| VALQUARIUS | 0.5 | 0.78 | 1.94 | 3.22 |
| VERNIA | 0.4 | 0.63 | 1.41 | 2.44 |
| VALQUARIUS | NS | 0.72 | 2.23 | 2.95 |
| VERNIA | 0.31 | 0.67 | 1.33 | 2.31 |
| VERNIA | 0.35 | 0.25 | 1.38 | 1.98 |
| VALQUARIUS | NS | 0.75 | 1.73 | 2.48 |
| VALQUARIUS | NS | 0.81 | 1.97 | 2.78 |
| VERNIA | 0.37 | 0.38 | 1.82 | 2.57 |
| VERNIA | 0.54 | 0.71 | 1.73 | 2.98 |
| VALQUARIUS | NS | 0.65 | 1.59 | 2.64 |
| VALQUARIUS | 0.33 | 0.56 | 1.80 | 2.69 |
| VERNIA | 0.42 | 0.25 | 1.93 | 2.60 |
| VALQUARIUS | NS | 0.68 | 2.20 | 2.88 |
| VALQUARIUS | NS | 0.67 | 2.77 | 3.44 |
| VERNIA | 0.33 | 0.85 | 1.08 | 2.26 |
| VALQUARIUS | NS | NS | 1.50 | 1.50 |
| VERNIA | NS | 0.50 | 0.83 | 1.33 |
| VALQUARIUS | NS | NS | 1.7 | 1.7 |
| VERNIA | NS | 0.78 | na | 0.78 |
| VALQUARIUS | NS | NS | 2.58 | 2.58 |
| VERNIA | 0.4 | 1.13 | 0.83 | 2.36 |
| VALQUARIUS | NS | NS | 2.2 | 2.2 |
| VERNIA | 0.15 | 0.75 | 1.08 | 1.98 |

NS - not significant fruit; na - data not available; * - control commercial rootstock
One box contains approximately 90 lbs. fruit.

BRIEF DESCRIPTION OF THE DRAWINGS

'UFR-1' is illustrated by the accompanying photographs, which show the tree's form, foliage, and fruit.

The colors shown are as true as can be reasonably obtained by conventional photographic procedures.

The photographs are of a tree approximately 10 years old. All figures were taken in the fall of 2013.

Figure 1:
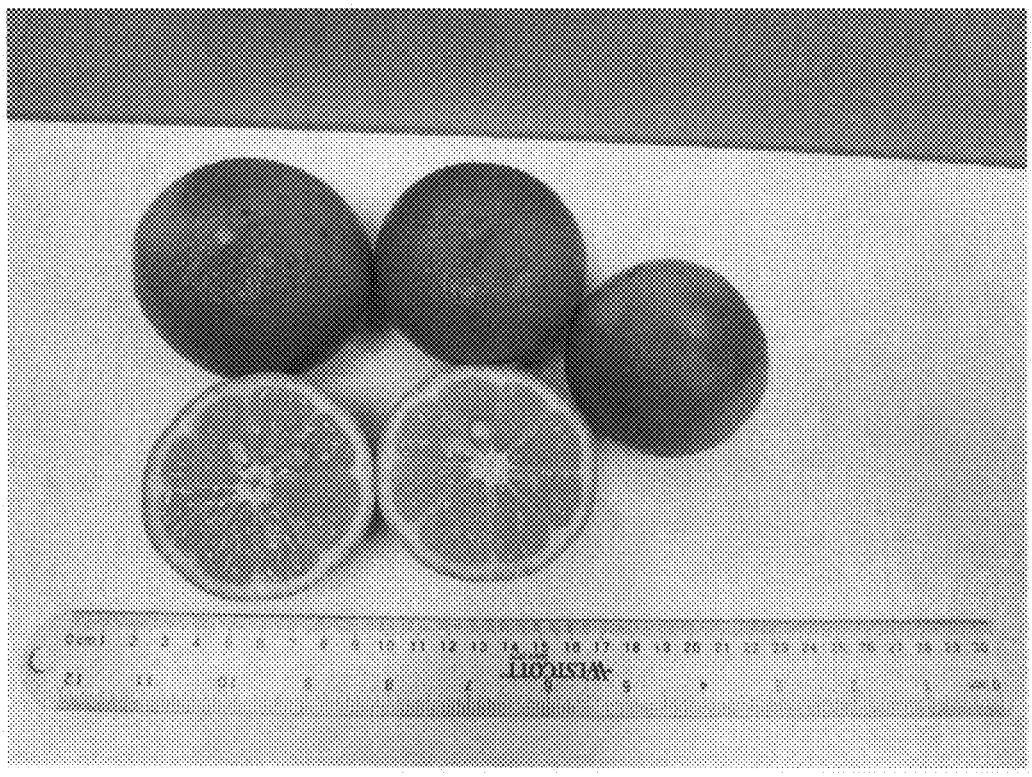

FIG. 1.—Shows a close-up of the nearly mature fruits with the rind and cross-sectional view of the fruit when cut in the center.

Figure 2:
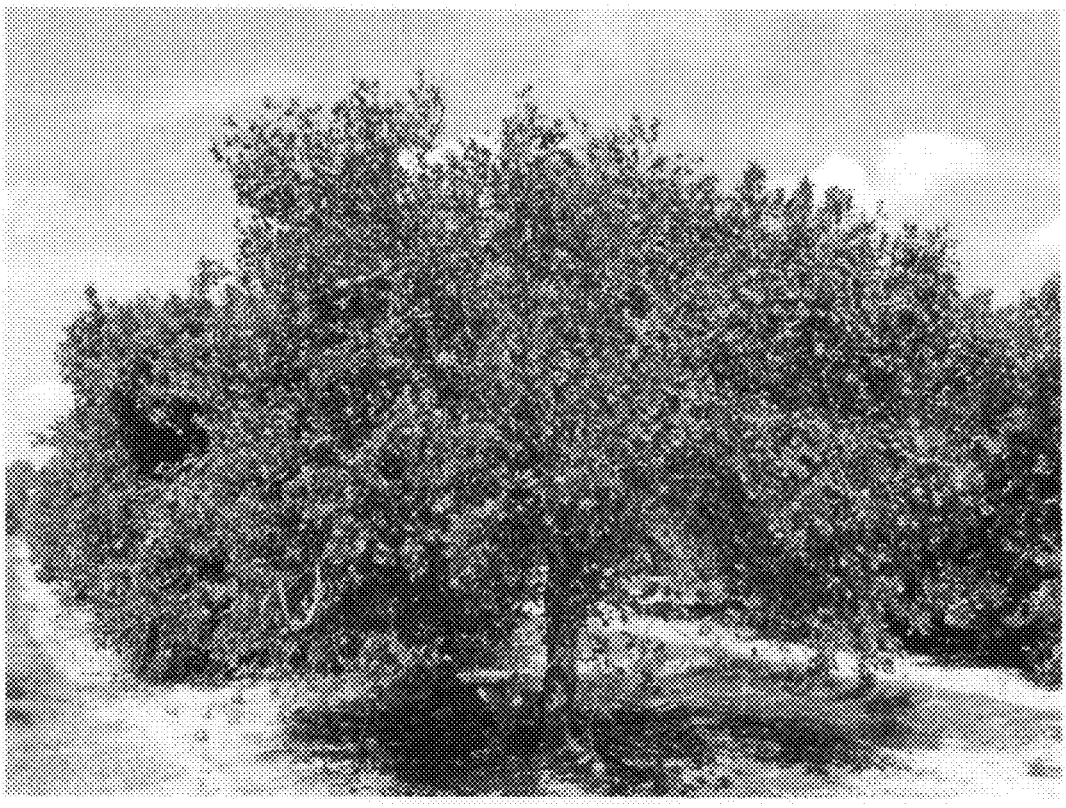

FIG. 2.—Shows the overall mature plant growth habit.

Figure 3:
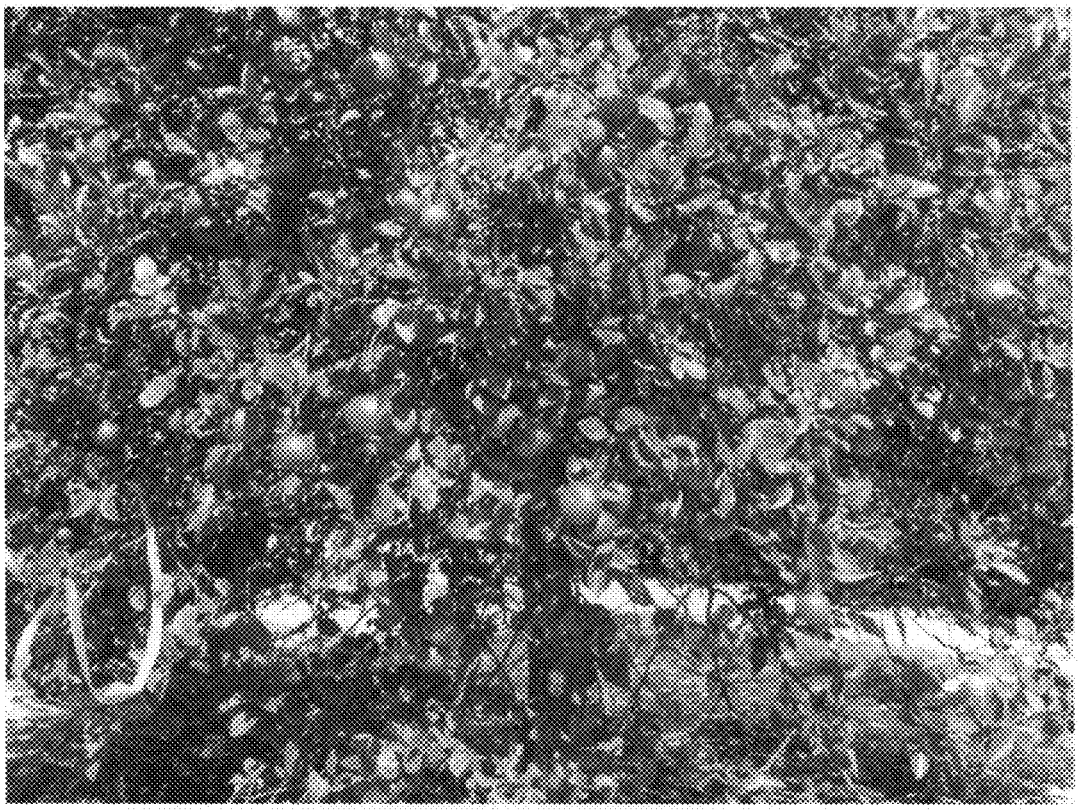

FIG. 3.—Shows a close-up of the mature growth habit.

Figure 4:
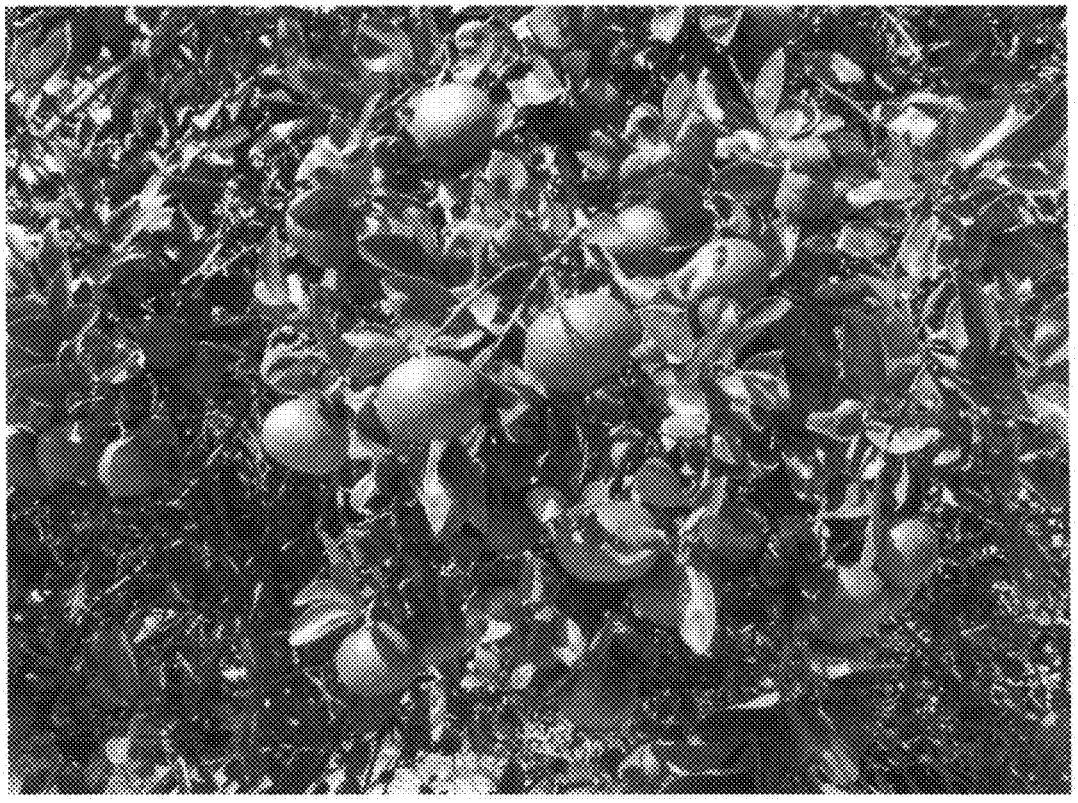

FIG. 4.—Shows leaves and nearly mature fruits.

Figure 5:
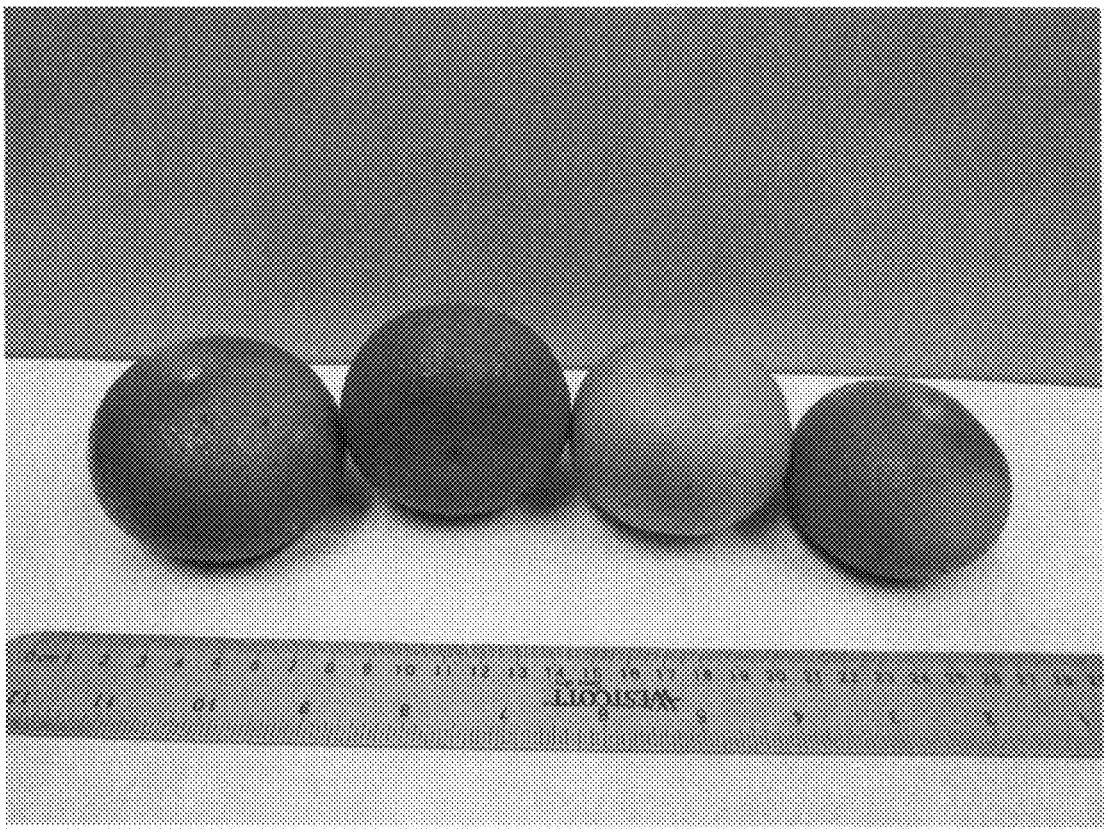

FIG. 5.—Shows a close-up of nearly mature fruits.

Figure 6:
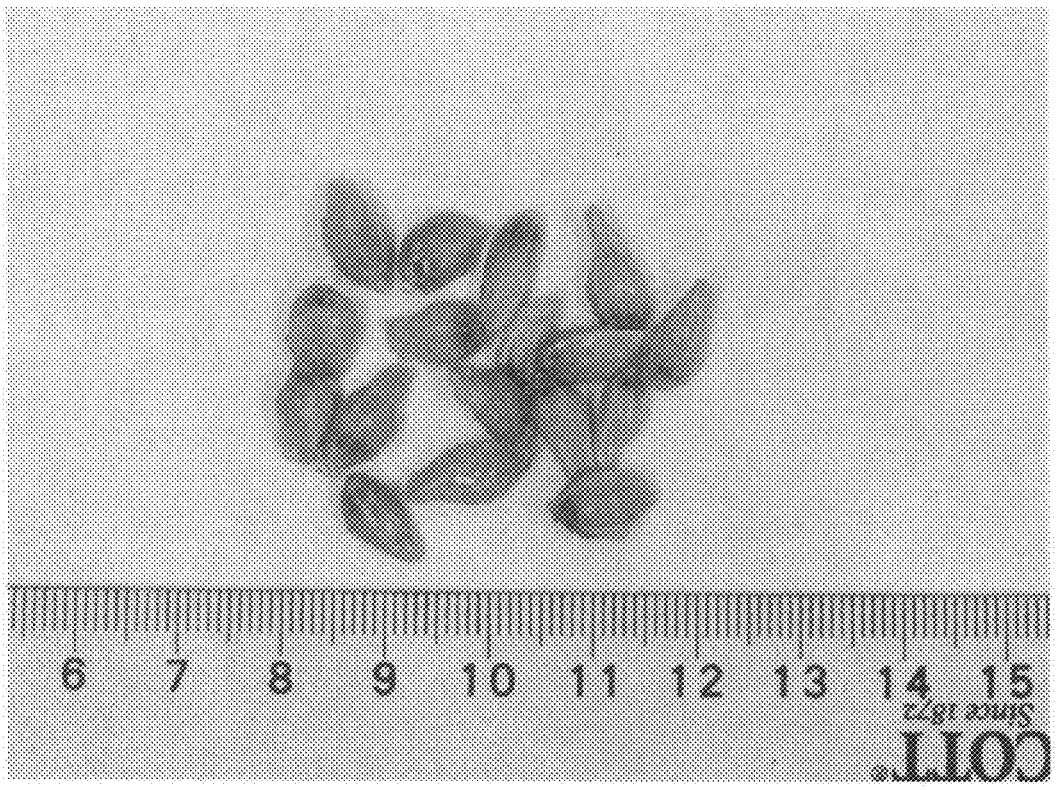

FIG. 6.—Shows a close-up of seeds from nearly mature fruit.

DETAILED BOTANICAL DESCRIPTION

The following detailed description sets forth the distinctive characteristics of 'UFR-1'. The colors (except those in common terms) are described from The R.H.S. Colour Chart published by The Royal Horticultural Society in London (second edition), in association with the Flower Council of Holland.

Phenotypic Description of *Citrus reticulata/Citrus paradisi+Citrus grandis×Citrus reticulata+Poncirus trifoliata* 'UFR-1'

Classification:

*Botanical*.—Complex allotetraploid hybrid rootstock ('Clementine' mandarin×'Orlando' tangelo) [*Citrus reticulata×Citrus paradisi*)+*Citrus grandis]×[Citrus reticulata+Poncirus trifoliata* (trifoliate orange)].

*Common name*.—Complex allotetraploid hybrid rootstock.

Parentage:

*Female parent*.—'Nova' mandarin+'Hirado Buntan' pummelo (zygotic seedling) somatic hybrid (unpatented).

*Male parent*.—'Cleopatra' mandarin+'Argentine' trifoliate orange; somatic hybrid (unpatented).

Tree:

*Ploidy*.—Tetraploid.

*Size*.—Medium-large.

*Height*.—3.65 meters.

*Tree spread*.—4.2 to 4.3 meters.

*Vigor*.—Moderately vigorous.

*Density*.—Canopies are moderately dense.

*Form*.—The tree is obloid-shaped with lateral and upright branches growing toward low to medium angles. Branches with fruit exhibit drooping.

*Growth habit*.—Both upright and lateral growth with a low to medium angle.

Trunk:

*Trunk diameter*.—19.5 cm in diameter at 30 cm above the ground on a 10-year-old tree.

*Trunk texture*.—Smooth.

*Trunk bark color*.—RHS 197A (greyed-green); irregularly striated with RHS N189A (green).

Branches:

*Crotch angle*.—First crotch forms 30- to 35-degree angle, middle crotch forms a 45-degree angle.

*Branch length*.—Branch reaches 2.7 meters from the first crotch to the tip of the branch.

*Branch texture*.—Relatively rough with small thorns or spines.

*Branch color* (*shoots from previous flush, hardened and* 4 *to* 5 *mm in diameter*).—RHS N137A (green).

Leaves:

*Size* (*lamina average*).—Length: 93.2 mm. Width: 51 mm. L/W ratio: 1.8.

*Thickness*.—Thicker than average diploid citrus rootstock hybrids.

*Type*.—Mostly simple leaf types, occasionally with bifoliate and trifoliate types of leaves appearing within the same tree.

*Shape*.—Elliptical.

*Apex*.—Retuse.

*Base*.—Acute to sub-obtuse.

*Margin*.—Entire and slightly undulate.

*Surface*.—Upper surface: Glabrous. Lower surface: Medium veins that are pinnately netted.

*Color*.—Upper surface (adaxial): RHS N137A (green). Lower surface (abaxial): RHS N137D (green).

*Petiole*.—Shape: Brevipetiolate (shorter than leaf lamina); junction between petiole and lamina is articulate. Width (petiole wing): Narrow. Shape (petiole wing): Obovate. Length: 14.4 to 18 mm. Width: 4.5 to 4.7 mm. Color: RHS N137A (green).

Flowers and flower buds:

*Type*.—Hermaphrodite.

*Bearing*.—Flowers grow from leaf axillaries and leaf terminals singly and in small clusters; most single flowers grow from leaf axillaries. Each flower branch consists of 4-10 flowers.

*Flower diameter*.—Fully open flower has an average diameter of 40.5 to 41 mm.

*Flower depth*.—Typical flower has an average depth of 21.5 mm.

*Flower blooming period*.—First bloom observed Mar. 8, 2014. Full bloom observed Mar. 15, 2014.

*Flower bud*.—Shape: Initial visible flower bud has a round ball shape; mature flower bud has an elongated olive shape. Initial visible flower bud size: Length: 3.2 mm in length. Diameter: 3.3 mm in diameter. Mature flower bud size: Length: 17.6 mm in length. Diameter: 10.5 mm in diameter. Color: RHS 144D (yellow-green) for initial visible flower bud; RHS NN155C (white) for mature flower bud, with RHS 150D (yellow-green) spots distributed at the tip of the flower bud.

*Flower petals*.—Shape: Flat, spatula-shaped. Apex shape: Smooth, acute-shaped. Base shape: Even obtuse. Length: 20 to 24 mm. Width: 10 to 10.5 mm. Thickness: 0.8 to 0.9 mm. Texture: Medium soft, smooth. Margin: Smooth. Color: Upper surface RHS NN155C (white); lower surface RHS NN155C (white), with RHS 150D (yellow-green) spots distributed toward to the petal apex.

*Flower sepal*.—Number: 5 per flower. Shape: Delta-shaped with an acute angle at the apex. Length: 4.6 mm. Width: 3.9 mm. Apex shape: Triangle-shaped. Margin: Smooth. Color: Upper surface RHS 154C (yellow-green); lower surface RHS 144D (yellow-green).

*Fragrance*.—Fragrant/Moderately fragrant.

*Flower pedicel*.—Length: 4.8 to 5.0 mm. Diameter: 1.4 to 1.5 mm. Color: RHS 144D (yellow-green).

*Reproductive organs*.—Fertility: Appears self-fertile. Pollen amount: Abundant/Moderate amount. Pollen color (general): Bright-yellow. Ovary shape: Oval-shaped.

Fruit:

*Size*.—Uniform.

*Height*.—50 to 55.8 mm on average.

*Width*.—66 to 75 mm on average.

*Average weight* (*per individual fruit*).—138 grams.

*Shape*.—Round.

*Shape* (*cross-section*).—Round.

*Apex*.—Truncated with slight dent.

*Apex cavity diameter*.—5.2 mm.

*Base cavity diameter*.—5.8 to 7.5 mm.

*Base*.—No neck.

*Harvesting*.—Fruit can be harvested from October through December in Florida.

*Fruit stem* (*short stem connecting the fruit*).—Length: 8.1 mm. Diameter: 4.9 mm. Color: RHS 143B (green) with RHS 195B (grey-green) strip.

Rind:

*Adherence*.—Adherence between albedo (mesocarp) and flesh (endocarp) is medium. The adherence is evenly distributed from base to apex.

*Thickness*.—3.4 to 4.8 mm on average.

*Texture*.—Smooth.

*Color*.—Flavedo (epicarp): Ranges between RHS 151B (yellow-green) to RHS 151A (yellow-green). Albedo (mesocarp): RHS 157D (green-white).

*Stylar end*.—Closed.

*Rind oil cell density*.—62 oil cells/square cm.

Flesh:

*Number of segments*.—Between 7 and 8 segments per fruit on average.

*Segment walls*.—Firm with sufficient strength to maintain integrity as separated.

*Juice*.—Abundant.

*Color*.—Uniformly RHS 11C (yellow).

*Texture*.—Soft.

*Vesicles*.—Length: Arranged from 13 to 15.6 mm on average. Diameter (thickness): 2.3 to 3.3 mm on average.

*Eating quality*.—N/A.

*Juice index*.—

*Soluble solids* (*average*).—9 Brix.

Seeds:

*Type*.—Polyembryonic.

*Number*.—Ranges from 4 to 16. Most fruit contains less than 10 seeds.

*Shape*.—Seed shapes are not uniform. Normal seeds are mostly ventricose/swollen-shaped and clavate club shaped.

*Size*.—Length: 14.5 to 16.4 mm. Width: 5.9 to 6.9 mm.

*Seed coat color*.—Outer Surface: RHS 155A (white) and wrinkled. Inner surface: RHS 164C (greyed-orange). Cotyledon color: RHS 145D (yellow-green).

Resistance to disease: 'UFR-1' rootstock was selected on the basis of its positive reaction to HLB disease (huanglongbing or citrus greening disease) in multiple field trials. Trees on this rootstock show a reduced frequency of infection and reduced disease symptoms once infected, as compared to commercial diploid rootstocks.

What is claimed is:

1. A new and distinct citrus rootstock cultivar as illustrated and described herein.

* * * * *